United States Patent
Li et al.

(10) Patent No.: US 11,022,666 B2
(45) Date of Patent: Jun. 1, 2021

(54) LOW-RANK TENSOR IMAGING FOR QUANTITATIVE MRI

(71) Applicant: Cedars-Sinai Medical Center, Los Angeles, CA (US)

(72) Inventors: Debiao Li, South Pasadena, CA (US); Anthony Christodoulou, Los Angeles, CA (US); Zhaoyang Fan, Hacienda Heights, CA (US); Zixin Deng, West Hollywood, CA (US); Nan Wang, Los Angeles, CA (US); Zhengwei Zhou, Los Angeles, CA (US); Sen Ma, Los Angeles, CA (US); Christopher Nguyen, Hollywood, CA (US); Yibin Xie, West Hollywood, CA (US); Jaime Shaw, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 89 days.

(21) Appl. No.: 16/406,977

(22) Filed: May 8, 2019

(65) Prior Publication Data

US 2019/0346523 A1    Nov. 14, 2019

Related U.S. Application Data

(60) Provisional application No. 62/668,720, filed on May 8, 2018.

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *G01R 33/5601* (2013.01);
(Continued)

(58) Field of Classification Search
CPC ............ G01R 33/5608; G01R 33/5601; G01R 33/56509; A61B 5/055
See application file for complete search history.

(56) References Cited

U.S. PATENT DOCUMENTS

| 6,560,353 B1 | 5/2003 | Haacke | |
| 7,005,854 B2 * | 2/2006 | Mitchell | G01R 33/56 324/307 |

(Continued)

OTHER PUBLICATIONS

Tucker, L., "Some mathematical notes on three-mode factor analysis," Psychometrika—vol. 31, pp. 279-311 (Sep. 1, 1966).
(Continued)

*Primary Examiner* — Dixomara Vargas
(74) *Attorney, Agent, or Firm* — Nixon Peabody LLP (57) ABSTRACT

A method of performing multidimensional magnetic resonance imaging on a subject comprises collecting imaging data for a region of interest of the subject, the imaging data related to one or more spatially-varying parameters of the subject within the region of interest; collecting auxiliary data for the region of interest in the subject, the auxiliary data related to one or more time-varying parameters of the subject within the region of interest; linking the imaging data and the auxiliary data; and constructing an image tensor with one or more temporal dimensions based on at least a portion of the linked imaging data and at least a portion of the linked auxiliary data.

22 Claims, 6 Drawing Sheets
(2 of 6 Drawing Sheet(s) Filed in Color)

(51) Int. Cl.
G01R 33/565 (2006.01)
G16H 30/40 (2018.01)
G01R 33/563 (2006.01)

(52) U.S. Cl.
CPC ...... *G01R 33/56509* (2013.01); *G01R 33/563* (2013.01); *G16H 30/40* (2018.01)

(56) References Cited

U.S. PATENT DOCUMENTS

| | | | | |
|---|---|---|---|---|
| 8,064,979 | B2* | 11/2011 | Salla | A61B 5/1107 600/407 |
| 9,404,986 | B2* | 8/2016 | White | G01R 33/48 |
| 9,482,732 | B2* | 11/2016 | Chesneau | G01R 33/56509 |
| 9,568,580 | B2* | 2/2017 | Dale | G01R 33/56341 |
| 9,684,979 | B2* | 6/2017 | Lu | G01R 33/4835 |
| 10,222,441 | B2* | 3/2019 | Kaditz | G01R 33/48 |
| 10,359,486 | B2* | 7/2019 | Kaditz | G01N 24/08 |
| 10,436,871 | B2* | 10/2019 | Li | A61B 5/055 |
| 2004/0249314 | A1* | 12/2004 | Salla | A61B 5/113 600/595 |
| 2004/0263169 | A1* | 12/2004 | Mitchell | G01R 33/56 324/309 |
| 2010/0142781 | A1 | 6/2010 | Walker | |
| 2015/0296214 | A1 | 10/2015 | Talib | |
| 2016/0232175 | A1 | 8/2016 | Zhou | |
| 2017/0221234 | A1 | 8/2017 | Chen | |
| 2017/0285122 | A1* | 10/2017 | Kaditz | G01R 33/448 |
| 2017/0285123 | A1* | 10/2017 | Kaditz | G01R 33/48 |
| 2018/0032128 | A1 | 2/2018 | Baranyi | |
| 2018/0306882 | A1* | 10/2018 | Li | G01R 33/56 |

OTHER PUBLICATIONS

De Lathauwer, L. et al., "A multilinear singular value decomposition," Siam J. Matrix Anal. Appl., vol. 21, No. 4, pp. 1253-1278 (Apr. 18, 2000).

Stanisz, G. et al., "T1, T2 relaxation and magnetization transfer in tissue at 3T," Magnetic Resonance in Medicine 54:567-512 (Aug. 5, 2005).

Kellman, P. et al., "Multicontrast delayed enhancement provides improved contrast between myocardial infarction and blood pool," Journal of Magnetic Resonance Imaging 22:605-613 (Oct. 7, 2005).

Liang, Z., "Spatiotemporal Imaging with partially separable functions," Dept. of Electrical and Computer Engineering, and Beckman Institute for Advanced Science and Technology, University of Illinois at Urbana-Champaign, pp. 988-991 (Apr. 12, 2007).

Adluru, G. et al., "Acquisition and reconstruction of undersampled radial data for myocardial perfusion MRI," J. Magn Reson Imaging, 29(2): 466-473. doi: 10.1002/jmri.21585 (Jan. 22, 2009).

Blume, U. et al., "Interleaved T1 and T2 relaxation time mapping for cardiac applications," Journal of Magnetic Resonance Imaging 29:480-487 (Jan. 22, 2009).

Pedersen, H. et al., "Temporally constrained k-t BLAST reconstruction using principal component analysis," Magnetic Resonance in Medicine 62:706-716 (Jul. 7, 2009).

Kolda, T. et al., "Tensor decompositions and applications," SIAM Review, vol. 51, No. 3, pp. 455-500 (Aug. 5, 2009).

Giri, S. et al., "T2 qualification for improved detection of myocardial edema," Journal of Cardiovascular Magnetic Resonance, pp. 1-13 (Dec. 30, 2009).

Liu, J. et al., "Respiratory and cardiac self-gated free-breathing cardiac CINE imaging with multiecho 3D hybrid radial SSFP acquisition," Magn Reson Med. May 2010; 63(5): 1230-1237 (Apr. 23, 2010).

Huang, C. et al., "T2 mapping from highly undersampled data by reconstruction of principal component coefficient maps using compressed sensing," Magn Reson Med. May 2010; 67(5): 1355-1366 (Aug. 16, 2011).

DiBella, E. et al., "Myocardial perfusion acquisition without magnetization preparation or gating," Magnetic Resonance in Medicine 67:609-613 (Dec. 21, 2011).

Liu, J. et al., "Tensor completion for estimating missing values in visual data," Arizona State University, VRViS Research Center, 8 pages (Jan. 24, 2012).

Xue, H. et al., "Phase-sensitive inversion recovery for myocardial T1 mapping with motion correction and parametric fitting," Magnetic Resonance in Medicine 69:1408-1420 (Jun. 26, 2012).

Trzasko, J. et al., "A unified tensor regression framework for calibrationless dynamic, multichannel MRI reconstruction," Mayo Clinic, Rochester, MN, United States, Proc. Intl. Soc. Mag. Reson. Med. 21, 1 page (Jan. 1, 2013).

Von Knobelsdorff-Brenkenhoff et al., "Myocardial T1 and T2 at 3T: reference values, influencing factors and implications," Journal of Cardiovascular Magnetic Resonance 2013, 15:53, 11 pages (Jun. 18, 2013).

Christodoulou, A. et al., "High-resolution cardiovascular MRI by integrating parallel imaging with low-rank and sparse modeling," Ieee Trans Biomed. Eng. Nov. 2013; 60(11): 3083-3092, 29 pages (Nov. 1, 2013).

Muehling, O. et al., "Regional heterogeneity of myocardial perfusion in healthy human myocardium: assessment wit magnetic resonance perfusion imaging," Journal of Cardiovascular Magnetic Resonance, vol. 6, No. 2, pp. 499-5074 (Jan. 1, 2014).

Sharif, B. et al., "Non-ECG-gated myocardial perfusion MRI using continuous magnetization-driven radial sampling," Magnetic Resonance in Medicine 72:1620-1628 (Jan. 7, 2014).

Lam, F. et al., "A subspace approach to high-resolution spectroscopic imaging," Magnetic Resonance in Medicine 71:1349-1357 (Feb. 4, 2014).

Yu, Y. et al., "Multidimensional compressed sensing MRI using tensor decomposition-based sparsifying transform," PLOS One, www.plosone.com, Jun. 2014, vol. 9, Issue 6, e98441 (Jun. 5, 2014).

Fu, M. et al., High-resolution dynamic speech imaging with joint low-rank and sparsity constraints, Magnetic Resonance in Medicine 73:1820-1832 (Jun. 9, 2014).

Pang, J. et al., "ECG and navigator-free four-dimensional whole-heart coronary MRA for simultaneous visualization of cardiac anatomy and function," Magnetic Resonance in Medicine 72:1208-1217 (Sep. 12, 2014).

Chen, D. et al., "Quantification of myocardial blood flow using non-ECG-triggered MR imaging," Magnetic Resonance in Medicine 74:765-771 (Sep. 16, 2014).

Kvernby, S. et al., "Simultaneous three-dimensional myocardial T1 and T2 mapping in one breath hold with 3D-QALAS," Journal of Cardiovascular Magnetic Resonance 2014, 16:102, 14 pages (Dec. 20, 2014).

Christodoulou, A., et al., "3D dynamic T1 mapping of the myocardium using a time-varying subspace," Proc. Intl. Soc. Mag. Reson. Med. 23, 1 page (Jan. 1, 2015).

Feng, L. et al., "XD-GRASP-Golden-angle radial MRI with reconstruction of extra motion-state dimensions using compressed sensing," Magnetic Resonance in Medicine 75:775-788 (Mar. 25, 2015).

Coolen, B. et al., "Three-dimensional quantitative T1 and T2 mapping of the carotid artery: Sequence design and in vivo feasibility," Magnetic Resonance in Medicine 75:1008-1017 (Apr. 28, 2015).

Akçakaya, M. et al., "Joint myocardial T1 and T2 mapping using a combination of saturation recovery and T2-preparation," Magnetic Resonance in Medicine 76:888-896 (Sep. 29, 2015).

Ma, C. et al., "High-resolution dynamic 31P-MRSI using high-order partially separable functions," Proc. Intl. Soc. Mag. Reson. Med. 24, 3 pages (Jan. 1, 2016).

Tamir, J. et al., "T2 shuffling: Sharp, multicontrast, volumetric fast spin-echo imaging," Magnetic Resonance in Medicine 77:180-195 (Jan. 20, 2016).

Hamilton, J. et al., "MR fingerprinting for rapid quantification of myocardial T1, T2 and proton spin density," Magnetic Resonance in Medicine 77:1446-1458 (Apr. 1, 2016).

He, J. et al., "Accelerated high-dimensional MR imaging with sparse sampling using low-rank tensors," IEEE Trans Med Imaging. Sep. 2016; 35(9): 2119-2129, 31 pages (Apr. 12, 2016).

(56) References Cited

OTHER PUBLICATIONS

Christodoulou, A. et al., "Fast dynamic electron paramagnetic resonance (EPR) oxygen imaging using low-rank tensors," Journal of Magnetic Resonance 270 (2016) 176-182 (Sep. 1, 2016).
Hou, M., "Tensor-based Regression Models and Applications"; Université Laval; Publication [online]. Oct. 2017 [retrieved Nov. 11, 2019]. Retrieved from internet: <URL: https://pdfs.semanticscholar.org/6252/52ad9a4bf89cb457175becd6e43a543efb80.pdf>; pp. 1-100.
International Search Report and Written Opinion for International Application No. PCT/US2019/51664, dated Dec. 2, 2019 (8 pages).
Christodoulou, A. et al., "Magnetic resonance multitasking for motion-resolved quantitative cardiovascular imaging," Nature Biomedical Engineering 2 (2018) 215-226 (Apr. 2018).
Cheng, J. A. et al., "Comprehensive multi-dimensional MRI for the simultaneous assessment of cardiopulmonary anatomy and physiology," Scientific Reports 7:5330 (Jul. 13, 2017).

\* cited by examiner

LOW-RANK TENSOR IMAGING FOR QUANTITATIVE MRI

CROSS-REFERENCE TO RELATED APPLICATIONS

This application claims priority to and the benefit of U.S. Provisional Patent Application No. 62/668,720, filed May 8, 2018, which is hereby incorporated by reference herein in its entirety.

TECHNICAL FIELD

The present disclosure relates MRI imaging. More specifically, the present disclosure relates to multidimensional MRI imaging utilizing full-rank image tensors and low-rank image tensors.

BACKGROUND

MRI imaging can be used to measure multiple varying dynamics of a subject ("multidimensional MRI imaging"). However, it can generally be difficult to resolve one varying dynamic (for example a $T_1$ relaxation parameter) in view of another varying dynamic (for example the movement of the subject's chest during respiration). Some solutions for these difficulties exists, such having the subject hold their breath during image to cease movement of the subject's chest. However, this method of multidimensional MRI imaging is still replete with issues. Aspects of the present disclosure address these and other difficulties.

SUMMARY

According to aspects of the present disclosure, a method of performing multidimensional magnetic resonance imaging on a subject comprises collecting imaging data for a region of interest of the subject, the imaging data related to one or more spatially-varying parameters of the subject within the region of interest; collecting auxiliary data for the region of interest in the subject, the auxiliary data related to one or more time-varying parameters of the subject within the region of interest; linking the imaging data and the auxiliary data; and constructing an image tensor with one or more temporal dimensions based on at least a portion of the linked imaging data and at least a portion of the linked auxiliary data.

According to additional aspects of the present disclosure, a method of constructing an image tensor comprises defining a cost function, the cost function taking a candidate image tensor as an argument; determining a minimum value of the cost function for one or more candidate image tensors; and selecting as the image tensor the candidate image tensor corresponding to the minimum value of the cost function; wherein the cost function penalizes discrepancies between (i) the candidate image tensor and (ii) the collected imaging data, the collected auxiliary data, or both the collected imaging data and the collected auxiliary data; and wherein the cost function penalizes larger values of (i) the rank of the candidate image tensor and (ii) the surrogate for the rank of the candidate image tensor.

According to aspects of the present disclosure, a system for performing multidimensional magnetic resonance imaging comprises a magnet operable to provide a magnetic field; a transmitter operable to transmit to a region within the magnetic field; a receiver operable to receive a magnetic resonance signal from the region with the magnetic field; and a process operable to control the transmitter and the receiver, the processor being configured to: collect imaging data for a region of interest of the subject, the imaging data related to one or more spatially-varying parameters of the subject within the region of interest; collect auxiliary data for the region of interest in the subject, the auxiliary data related to one or more time-varying parameters of the subject within the region of interest; link the imaging data and the auxiliary data; and construct an image tensor with one or more temporal dimensions based on at least a portion of the linked imaging data and at least a portion of the linked auxiliary data.

According to additional aspects of the present disclosure, a system for constructing an image tensor comprises a magnet operable to provide a magnetic field; a transmitter operable to transmit to a region within the magnetic field; a receiver operable to receive a magnetic resonance signal from the region with the magnetic field; and a processor operable to control the transmitter and the receiver, the processor being configured to define a cost function, the cost function taking a candidate image tensor as an argument; determine a minimum value of the cost function for one or more candidate image tensors; and select as the image tensor the candidate image tensor corresponding to the minimum value of the cost function; wherein the cost function penalizes discrepancies between (i) the candidate image tensor and (ii) the collected imaging data, the collected auxiliary data, or both the collected imaging data and the collected auxiliary data; and wherein the cost function penalizes larger values of (i) the rank of the candidate image tensor and (ii) the surrogate for the rank of the candidate image tensor.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other advantages of the present disclosure will become apparent upon reading the following detailed description and upon reference to the drawings.

While the present disclosure is susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure has been described with reference to one or more particular embodiments or implementations, those skilled in the art will recognize that many changes may be made thereto without departing from the spirit and scope of the present disclosure. Each of these embodiments or implementations and obvious variations thereof is contemplated as falling within the spirit and scope of the present disclosure. It is also contemplated that additional embodiments implementations according to aspects of the present disclosure may combine any number of features from any of the embodiments described herein.

Magnetic resonance-based imaging (MR imaging) is a technique most often used for imaging the human body that takes into account principles of nuclear magnetic resonance. For example, doctors and other medical professionals often use MR imaging to view tissue within the human body. Nuclear magnetic resonance is a phenomenon in which nuclei (such as protons in body tissue) localized in a magnetic field emit energy that can be detected. This energy that is detected can be used to create an image. MR imaging generally involves two principle steps. First, the magnetic moment of the nuclei (caused by the intrinsic spin property of elementary particles) are aligned (or polarized) by the presence of an external magnetic field. While in the presence of this external magnetic field, the magnetic moment of each nuclei will generally precess about an axis parallel to the magnetic field. The rate of this precession w is generally proportional to $\gamma B_0$, where $B_0$ is the magnitude of the external magnetic field, and y is the gyromagnetic ratio of the nuclei, which is the ratio the nuclei's magnetic moment to its angular momentum. The rate of the precession w is considered the nuclei's resonant frequency.

The second principle step in MR imaging is to apply an electromagnetic pulse sequence (usually a radiofrequency, or RF, pulse) to the nuclei. When the frequency of the RF pulses sequence is generally equal to the resonant frequency of the nuclei, the nuclei absorb the energy of the RF pulse and the magnetic moments are rotated out of alignment with the magnetic field. The magnetic moments of the excited nuclei eventually re-align within the presence of the external magnetic field in a process known as relaxation, which has two components. $T_1$ relaxation describes how the component of the magnetic moment parallel to the external magnetic field returns to its initial value. $T_2$ relaxation describes how the components of the magnetic moment perpendicular to the external magnetic field return to their initial value. Because the magnetic moments of nuclei in the external magnetic field without the RF pulse sequence applied are generally parallel to the external magnetic field, $T_1$ relaxation generally describes how parallel component of the magnetic moment returns to its maximum value, while $T_2$ relaxation generally describes how the perpendicular components of the magnetic moment decay. The nuclei of different material relax at different rates and thus emit differing signals, which can be detected and used to form an image identifying the different materials.

Quantitative MR imaging is an application of NMR principles that aims to quantify some characteristic of the tissue being imaged. For example, practitioners may wish to quantify $T_1$ values to detect anomalies such as scar tissue, $T_2$ values to detect tumors, the speed of a contrast agent advancing through tissue to detect ischemia, or diffusion-based characteristics to detect abnormal fiber structure. However, imaging in the presence of various overlapping dynamics—both physiological (e.g. cardiac and respiratory motion) and physical (e.g. $T_1$ and $T_2$ relaxation)—is a major technical challenge. For example, it may be difficult to utilize multiple different $T_1$-weighted images to analyze $T_1$ values of tissue in the abdomen, because the patient's breathing has caused the physical location of the tissue being imaged to change.

Figure 1:
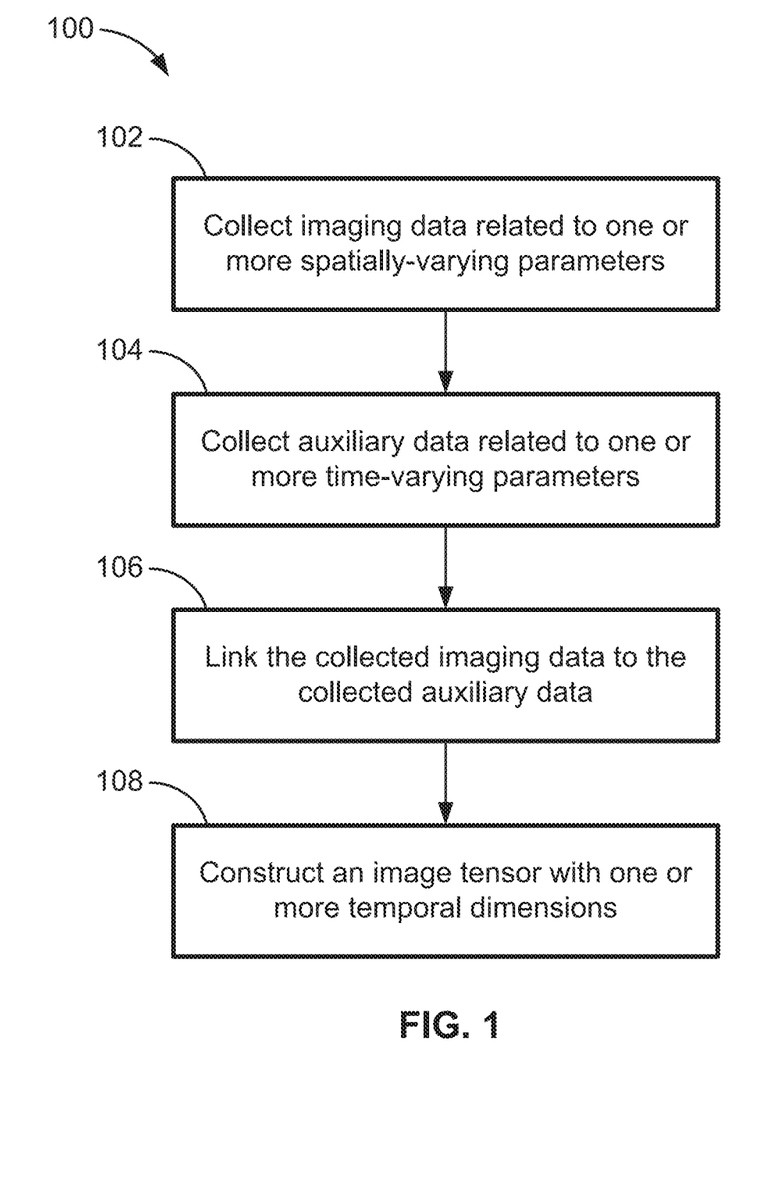
FIG. 1 illustrates a method of performing multidimensional magnetic resonance imaging, according to aspects of the present disclosure.

Referring now to FIG. 1, a method 100 of performing magnetic resonance imaging on a subject is shown. At step 102, imaging data of the subject/patient is collected using an MRI equipment. Generally, the imaging data is from a specific region of interest of the subject. In an example, the region of interest could be the subject's abdomen or chest. In other examples, the region of interest of the subject is more specific. For example, the region of interest could be an organ, such as the subject's liver, lungs, heart, pancreas, brain, prostate, breast, or any other organ. The imaging data is dependent on or related to one or more varying parameters of the region of interest of the subject. These parameters can include relaxation parameters such as $T_1$, $T_{1p}$ (also known as T1-rho), $T_2$, or $T_2$* (also known as T2-star). The parameters can also include a contrast agent kinetic parameter, a diffusion parameter (which includes changing strength, changing direction, or both), elastographic wave propagation, dynamic contrast enhancement, magnetization transfer, chemical exchange saturation transfer, free induction decay, flow, cardiac motion, respiratory motion, or the general passage of time.

These parameters can be spatially-varying or time-varying, and some of the parameters can vary across both space and time. For example, cardiac motion is generally a time-varying parameter, while the relaxation parameters, the contrast agent kinetic parameter, and the diffusion parameter are generally time-varying. Generally, the imaging data is indicative of the value or magnitude of the spatially-varying parameters.

In an example, the region of interest is the subject's abdomen containing their liver, and the spatially-varying parameter that is being measured is the $T_1$ relaxation parameter. The $T_1$ relaxation parameter can be spatially-varying, meaning that the value of the $T_1$ relaxation parameter at a first physical location within the subject's liver can be different than the value of the $T_1$ relaxation parameter at a second physical location within the subject's liver. In a resulting image showing the value measured $T_1$ relaxation parameter, different locations in the image (corresponding to different physical locations within the subject's liver) will show different values. In some implementations, the spatially-varying parameters can also be time-varying. In other implementations, the spatially-varying parameters can additionally or alternatively be related to physical motion of the region of interest of the subject. In general, the techniques disclosed herein can be used to perform multidimensional imaging that resolves parameters that can vary across space and time.

To collect the imaging data, an RF pulse sequence is applied to the region of interest of the subject. The resulting signal(s) are then measured. Thus, the RF pulse sequence may be designed using saturation recovery pulses to measure $T_1$ relaxation, $T_2$ prep pulses to measure $T_2$ relaxation, or any other specific pulse sequence to measure a specific spatially-varying parameter or combination of spatially-varying parameters. There is generally a pause after each RF pulse of the RF pulse sequence to allow for the resulting signal to be measured. In some implementations, the imaging data is collected in a semi-continuous mode. In the semi-continuous mode, the RF pulse sequence contains additional pauses to allow the $T_1$ signal to recover (as measurement can reduce/saturate the $T_1$ signal). In other implementations, the imaging data is collected in a continuous mode, where the applied RF pulse sequence is not paused to allow the $T_1$ signal to recover, and only contains pauses to allow for measurement of the resulting signal. In either implementation, the applied RF pulse sequence is not paused to wait for any particular respiratory position, but rather the subject is allowed to breathe freely.

At step 104, auxiliary data is obtained from the subject. The auxiliary data is related to one or more time-varying parameters of the region of interest of the subject, and is generally indicative of the value or magnitude of the time-varying parameters. In some implementations, the auxiliary data is collected simultaneously with the imaging data. In other implementations, the auxiliary data is collected before or after the imaging data. The time-varying parameters measured by the auxiliary data can be related to the physical position of different structures within the subject. For example, one time-varying parameter is the position of the subject's chest or abdomen during a respiratory cycle, e.g. while the patient is breathing. In some implementations, the auxiliary data can take the form of an external respiratory gating signal. In this implementations, the time-varying parameter measured by the auxiliary data is the position of the chest wall. In other implementation, the auxiliary data can take the form of a respiratory navigator signal, which can measure the position of the subject's liver dome. In additional implementations, the auxiliary data can take the form of training data interleaved with the imaging data. In these implementations, the training data is generally a subset of the imaging data (which measures spatially-varying parameters) which differs only in the time at which it was obtained. This subset of imaging data is generally measured at a rate which is sufficient to resolve any motion of the region of interest.

In step 106, the collected imaging data is linked with the collected auxiliary data to correlate the spatially-varying parameters with the time-varying parameters. At this step, the imaging data and the auxiliary data are analyzed such that the data points comprising the values of the spatially-varying parameters are correlated with one or more corresponding data points comprising the values of one or more of the time-varying parameters. The corresponding data point of the auxiliary data is indicative of a time when the corresponding data point of the imaging data was measured. In an example, the spatially-varying parameter being measured is the $T_1$ relaxation parameter, while the time-varying parameters being measured are the position of the subject's chest during respiration and the position of the subject's liver dome. By linking the imaging data and the auxiliary data, a given data point that measures the $T_1$ relaxation parameter can be linked to a position of the subject's chest and a position of the subject's liver dome. Thus, by linking the imaging data and the auxiliary data, the time period in which a given data point for one of the parameters was measured can be determined, and the value of the other parameters during that time period can be determined. In some implementations, this time period is less than or equal to the sampling period of the auxiliary data. The sampling period can be generally less than about 50 ms when the region of interest is the subject's heart, and can be generally less than about 200 ms when the region of interest is elsewhere.

At step 108, an image tensor with one or more spatially-varying dimensions and one or more time-varying dimensions is constructed from the imaging data and the auxiliary data. This image tensor contains images that are constructed from the collected and linked data. Thus, any given image can show the value of the spatially-varying parameter across the region of interest that was imaged, and can indicate the time period in which the imaging data was collected and the value of the one or more time-varying parameters at that time period. The images are arranged according to common attributes. For example, the constructed image tensor may have three dimensions. If this image tensor is visualized, the first dimension can be along the x-axis and correspond to the $T_1$ relaxation parameter (spatially-varying), the second dimension can be along the y-axis and correspond to the position of the chest during respiration (time-varying), and the third dimension can be along the z-axis and correspond to the position of the liver dome during respiration (time-varying). In this example, every image along the x-axis for a given position along the y-axis and the z-axis will show the value of the $T_1$ relaxation parameter measured at different times, but having the same value along the y-axis and the z-axis, e.g. the position of the chest is the same for each image and the position of the liver dome is the same for each image. The same holds true for images spaced along the other two dimensions.

The construction of the image tensor can pose a two-fold problem. First, the image tensor needs to be consistent with the collected data and thus properly describe the region of interest that was analyzed. Second, to reduce artifacts and noise, the image tensor generally needs to be of low-rank or be a full-rank tensor that can be sufficiently approximated by a low-rank tensor. Full-rank tensors are tensors that produce a full-rank matrix when unfolded or flattened along each of its dimensions. A full-rank matrix is a matrix whose rows or columns (whichever is fewer in amount) are linearly independent. Low-rank tensors are tensors that produce a low-rank matrix when unfolded or flattened along at least one of its dimensions. A low-rank matrix is a matrix whose rows and columns are linearly dependent.

With respect to the image tensor, low-rank tensors are generally image tensors where the spatially-varying parameters and the time-varying parameters are able to be accurately described with fewer imaging data points and auxiliary data points than tensor elements. Images in a low-rank tensor are generally always linearly independent, which is not necessarily true for a full-rank tensor. Low-rank tensors thus can be decomposed into smaller factors without information loss as compared to a full-rank tensor. In some implementations, construction of the image tensor includes selecting an image tensor that is low-rank or full-rank, and can be sufficiently approximated by a low-rank image tensor. In other implementations, construction of the image tensor includes identifying a plurality of tensor factors based on at least a portion of the collected and linked imaging data, and at least a portion of the collected and linked auxiliary data, and combining at least a portion of the identified plurality of tensor factors.

Figure 2:
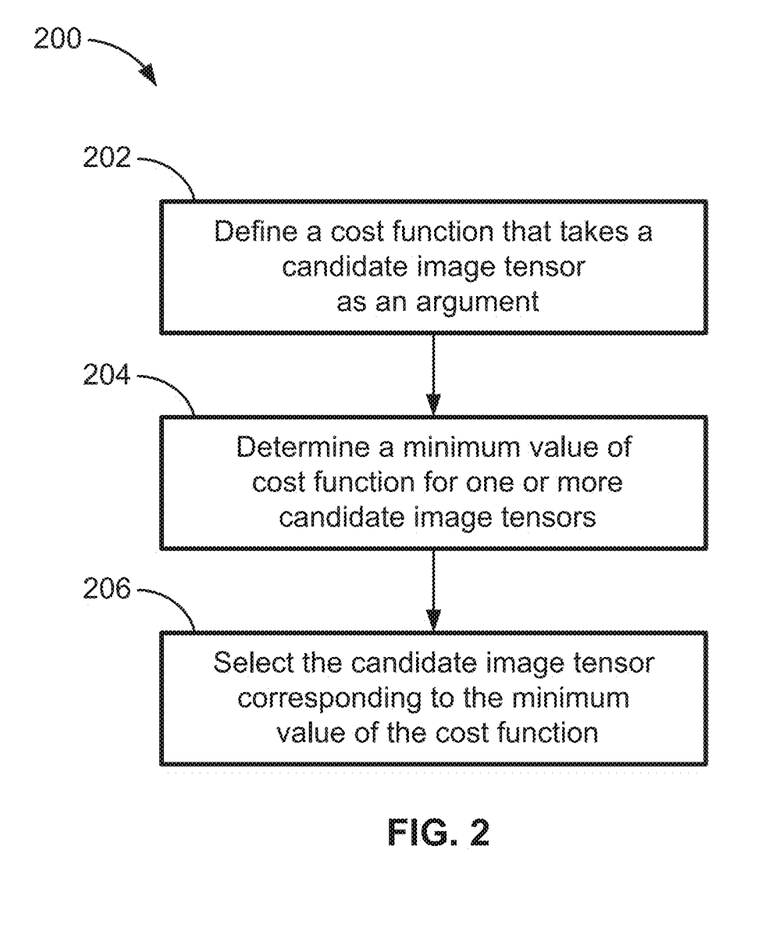
FIG. 2 illustrates a method of constructing an image tensor, according to aspects of the present disclosure.

Referring now to FIG. 2, a method 200 constructing the image tensor is shown. In step 202, a cost function is defined. The argument of the cost function is any image tensor that could be selected as the image tensor to be used to imaging and analysis purposes, referred to as a candidate image tensor. Candidate image tensors are image tensors that are low-rank or full-rank, and can be approximated by a low-rank image tensor. The cost function takes as input a candidate image tensor and produces an output that is indicative of (i) how consistent the candidate image tensor is with the collected data and (ii) how strongly interrelated the images of the candidate image tensor is. More specifically, the cost function penalizes discrepancies between (i) the candidate image tensor and (ii) the collected imaging data, the collected auxiliary data, or both the collected imaging data and the collected auxiliary data. The cost function also penalizes large values of (i) the rank of the candidate image tensor or (ii) the surrogate for the rank of the candidate image tensor. This surrogate for the candidate image tensor measures how well the candidate image tensor can be approximated by a low-rank image tensor. In essence, the surrogate measures how close the candidate image tensor is to a low-rank tensor. In some implementations, a candidate image tensor can itself be a low-rank image tensor. In some implementations, a candidate image tensor can be a full-rank image tensor that can be approximated by a low-rank image tensor to a certain degree.

In some implementations, the surrogate for the rank of the candidate image tensor is determined using a metric based on the nuclear norm of the candidate image tensors, the Schatten p-norm of the candidate image tensors, or the Ky Fan k-norm of the candidate image tensors. Other metrics can be used as well.

The cost function is generally given by the following equation:

$$f(\chi)=\|d-E(\chi)\|_2^2+R(\chi).$$

Here, $\chi$ is a candidate image tensor; d is a vector that includes the collected imaging data, the collected auxiliary data, or both the collected imaging data and the collected auxiliary data; $E(\chi)$ represents the spatial encoding mechanism and measurement used to obtain the data; and $R(\chi)$ is the value of the surrogate for the rank of the candidate image tensor, plus any additional regularization factor imposing structural assumption on x, such as transform sparsity.

The spatial encoding mechanism that is used include Cartesian spatial encoding; non-Cartesian spatial encoding such as radial, spherical, stack-of-stars, spirals, cones, stack-of-spirals, and arbitrary k-space trajectories; and hybrid encoding mechanisms that could include switching between Cartesian and non-Cartesian spatial encoding. In some implementations, the encoding mechanism incorporates a motion-mimicking operator so as to compensate for any motion of the region of interest of the subject.

In some implementations, $R(\chi)$ is the rank of the candidate image tensor itself. The quantity $\|n\|_2^2$ represents the squared 2-norm or squared Euclidean distance of the argument vector n, which is equal to the sum of the squared absolute values of the elements of n. Other norms or distance measurements can be used as well.

At step 204, a minimum value of the cost function for one or more candidate image tensors is determined. Because the cost function simply adds (i) the magnitude of the discrepancy between the collected data and the candidate image tensor and (ii) the value of the surrogate for the rank of the candidate image tensor, the candidate image tensor with the minimum value of the cost function is the candidate image tensor that is the most consistent with the collected data and can be best approximated by a low-rank image tensor. In some implementations, the cost function is minimized using a convex optimization technique, such as an alternation direction of multipliers algorithm or a singular value thresholding algorithm. In other implementations, the cost function is minimized using a non-convex optimization technique such as power factorization.

At step 206, the candidate image tensor corresponding to the minimum value of the cost function is selected as the image tensor of step 108. Generally, the candidate image tensor that is selected is either a low-rank image tensor or a full-rank image tensor that is closest to being a low-rank image tensor, while also remaining consistent with the collected imaging data, the collected auxiliary data, or both the collected imaging data and the collected auxiliary data. In this manner, the selected candidate image tensor generally has a minimum rank as compared to other candidate image tensors, or has a minimum value of a surrogate for the rank when compared to other candidate image tensors. In some implementations, all of the candidate image tensors are generally consistent with the collected data to an equal level, and thus the image tensor that is constructed is the image tensor that can be sufficiently approximated by a low-rank image tensor having a minimum rank or minimum value of the surrogate for the rank of the candidate image tensor. In other implementations, all of the candidate image tensors that are generally consistent with the collected data to an equal level are full-rank, and thus the image tensor that is constructed is the low-rank image tensor that is the best approximation of the full-rank image tensor which retains consistency with the collected data.

Figure 3A:
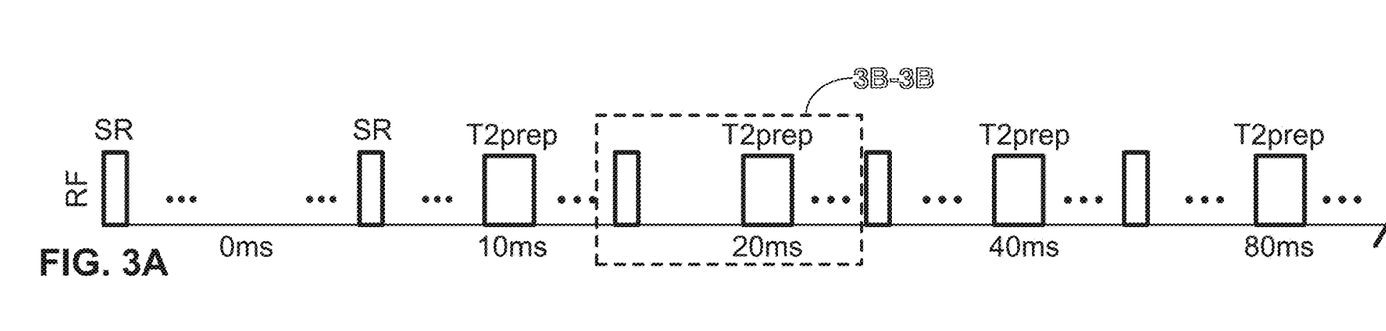
FIG. 3A illustrates an implementation of a pulse sequence used to perform multidimensional magnetic resonance imaging, according to aspects of the present disclosure.
Figure 3B:
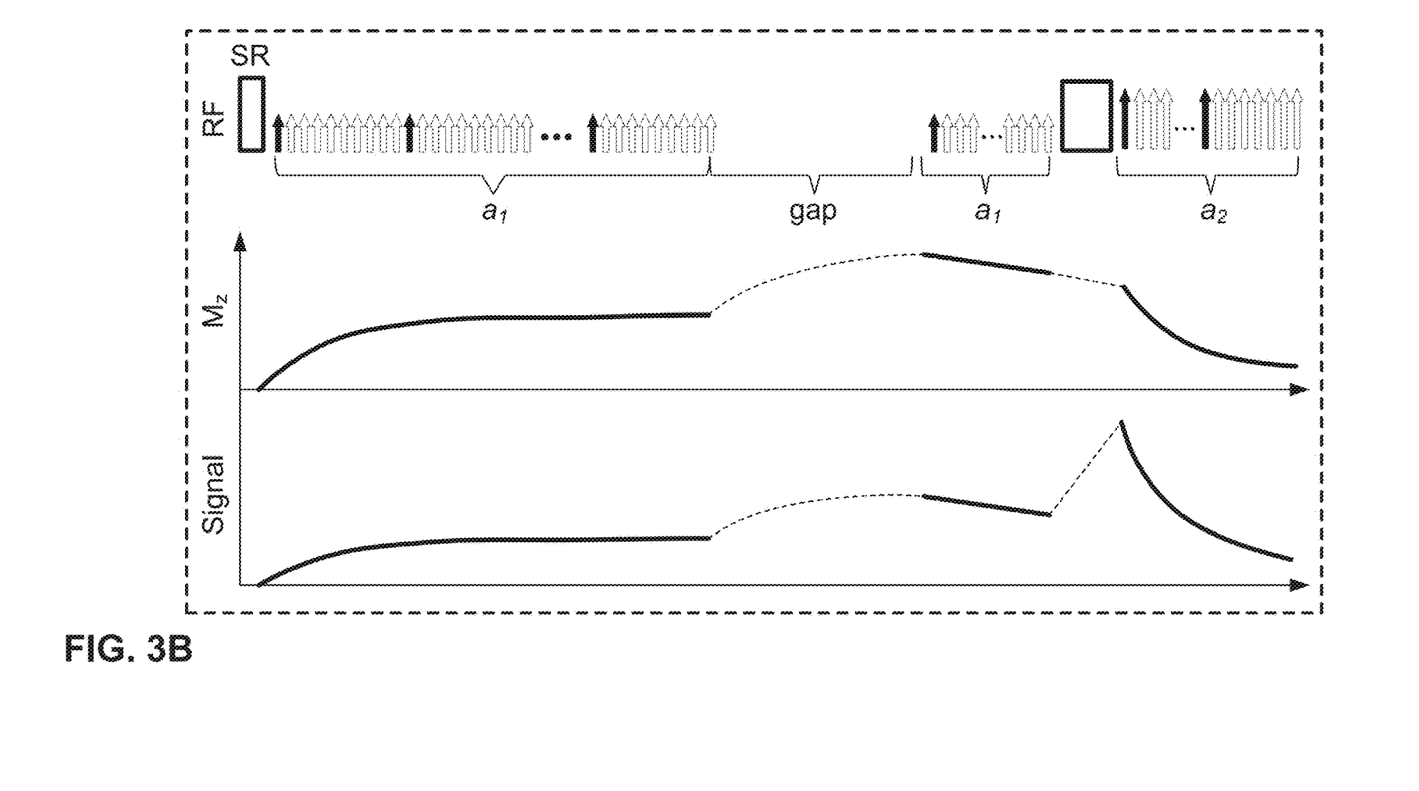
FIG. 3B illustrates a zoomed-in view of a portion of the pulse sequence of FIG. 3A, according to aspects of the present disclosure.

Referring now to FIG. 3A and FIG. 3B, an implementation of a single scan used to obtain data is shown. FIG. 3A illustrates the RF pulse sequence, which includes a plurality of saturation recovery (SR) pulses interleaved with a plurality of $T_2$-preparation (T2prep) modules. The SR pulses are used to measure the $T_1$ recovery time of the region of interest, while the T2prep modules are used to measure the $T_2$ recovery time of the region of interest. The duration of the T2prep modules can vary between 0 ms, 10 ms, 20 ms, 40 ms, 80 ms, and other values.

FIG. 3B illustrates a zoomed-in view of a single cycle containing one SR pulse and one T2prep module. As shown, after the SR pulse, imaging data is measured repeatedly. The darkened arrows show data points that are encoded in the same fashion such that the only thing that is different is the temporal aspect of the data point, e.g. the time when the data point was collected. The measurement of data following an SR pulse can also include a gap where no data is measured to allow the $T_1$ magnetization to recover. The z-axis magnetization and the measured signal are also illustrated. In some implementations, a flip angle of $\alpha_1=8$ degrees is used during the SR phase, while a flip angle of $\alpha_2=16$ degrees is used during the T2prep phase.

Figure 4:
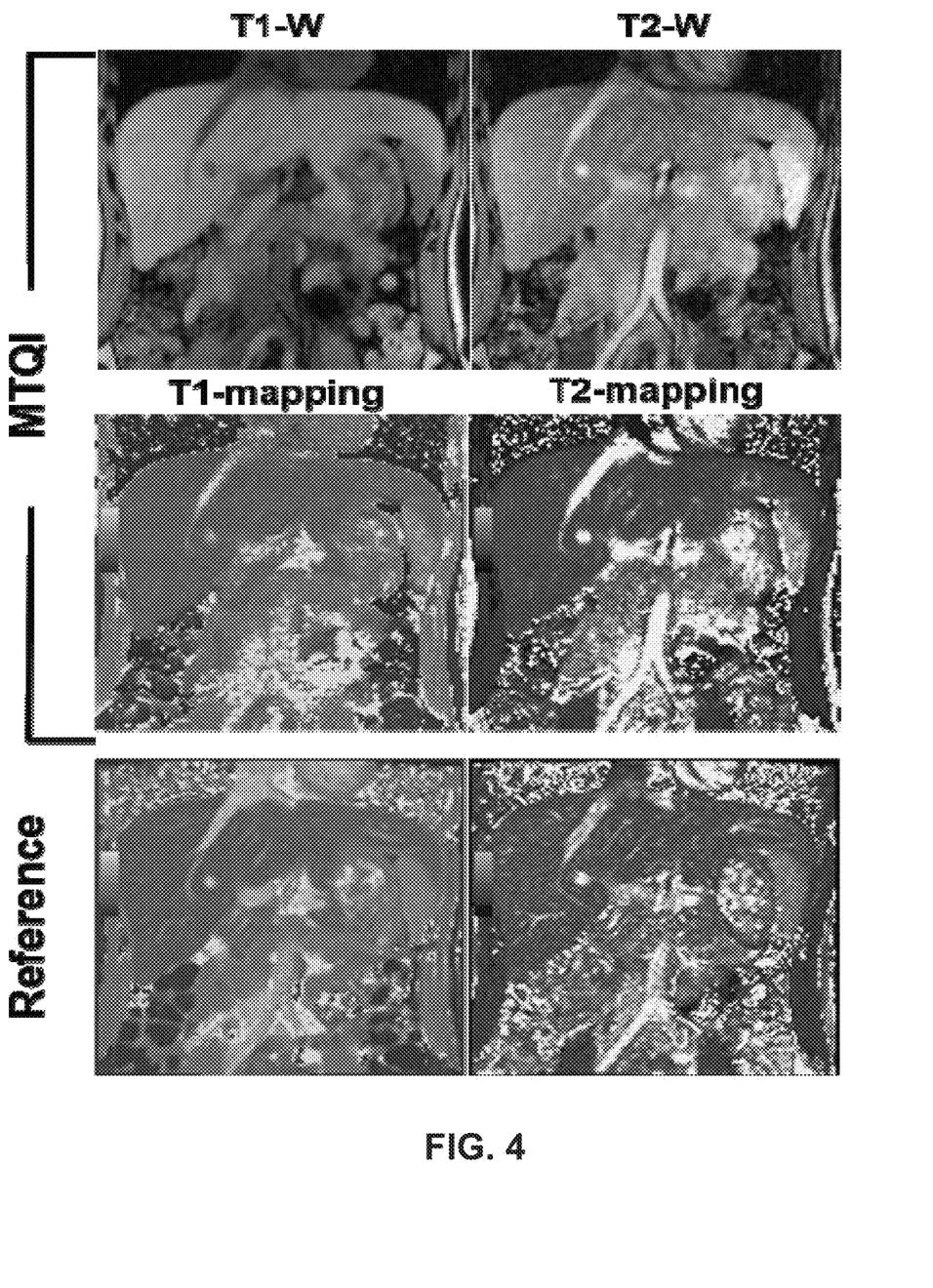
FIG. 4 shows a comparison between $T_1$-weighted and $T_2$-weighted images obtained according to the methods of FIG. 1 and FIG. 2, $T_1$-weighted and $T_2$-weighted maps obtained according to the methods of FIG. 1 and FIG. 2, and $T_1$-weighted and $T_2$-weighted reference images obtained according to conventional methods, according to aspects of the present disclosure.

Referring now to FIG. 4, a $T_1$-weighted image and a $T_1$ map obtained using the principles described herein is compared to a reference $T_1$ map obtained using conventional breath-holding techniques. Similarly, a $T_2$-weighted image and a $T_2$ map obtained using the principles described herein is compared to a reference $T_2$ map. As is shown, the $T_1$ and the $T_2$ map obtained using the principles described herein is generally comparable to the reference maps.

In some implementations, the imaging data and the auxiliary data are obtained using a stack-of-stars acquisition. In these implementations, radial projections are continuously acquired, for example during the saturation-recovery phases (after SR pulses), and during the $T_2$ prep phases (after T2prep modules). These projections can be acquired with in-plane golden angle ordering and Gaussian-density randomized partition ordering. In some implementations, the external magnetic field has a strength of about 1.5 T, or between greater than 0 T and less than about 3.0 T. In some implementations, the principles described herein can be used as a 4D-MRI approach for radiotherapy planning with a tumor-tailored image contrast. In some implementations, a 2D scan using the principles described herein can last for about one minute, while a 3D scan using the principles described herein can last for about ten minutes. The MTQI principles described herein can be used to measure dynamics such as diffusion weighted imaging and apparent diffusion coefficient mapping.

A variety of different motion compensation techniques can be used to adjust for motion of the region of interest of the subject. Any movement of the region of interest (such as the subject breathing) modifies the collected data in a manner that must be compensated for. In one implementation, imaging data related to one or more spatially-varying parameters is collected, and auxiliary data related to only a single time-varying parameter is collected. The time-varying parameter is the elapsed time t. Image registration techniques are then used to estimate a spatial transformation that describes motion that occurs as a function of any of the desired time-varying parameters. For example, a spatial transformation can be used to approximate respiratory motion as a function of elapsed time or as a function of the respiratory phase.

For simple spatial transformations such as translation and rotation, the spatial transformation can be applied directly to the imaging data and/or the auxiliary data to compensate for the movement. The modification of the imaging and/or auxiliary data effectively inverts the movement that took place during the imaging sequence, which thus reduces the effect of motion. For more complicated spatial transformations such as non-rigid motion, the spatial transformation can be incorporated into the cost function that would otherwise only describes spatial encoding. In either implementation, once (i) the spatial transformation is applied to the imaging data and/or the auxiliary data or (ii) the spatial transformation is incorporated into the cost function, construction of the image tensor proceeds as discussed herein.

Figure 5:
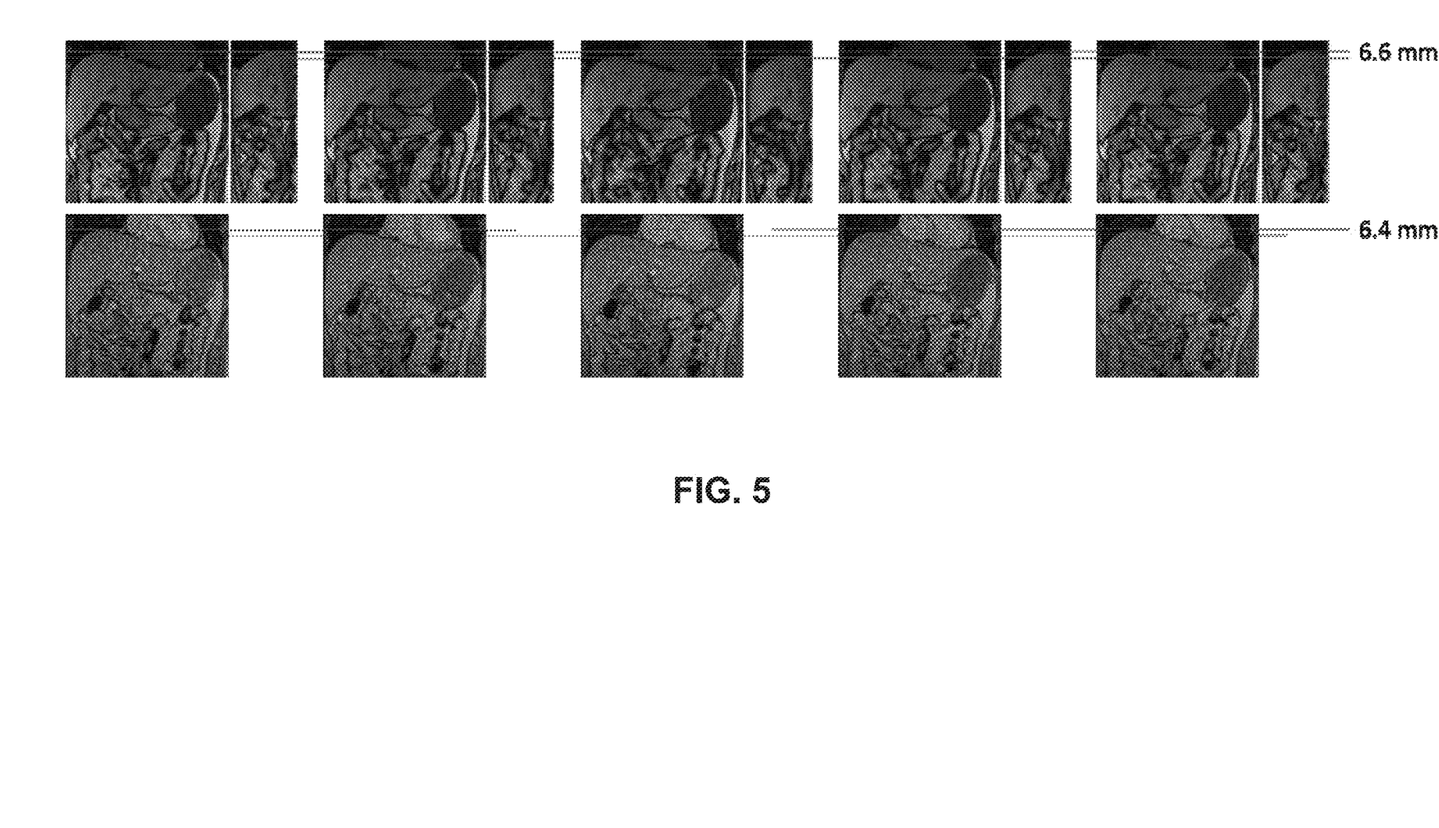
FIG. 5 shows a comparison between the movement amplitude revealed by obtaining images according to the methods of FIG. 1 and FIG. 2, and the movement amplitude by obtaining images according to conventional methods, according to aspects of the present disclosure.

Referring now to FIG. 5, motion-resolved three-dimensional $T_1$ weighted images obtained according the principles described herein are compared to real-time two-dimensional images obtained according to conventional methods. The upper row of images in FIG. 5 illustrates coronal and sagittal views obtained using the principles described herein, and reveal a motion amplitude of about 6.6 millimeters. This is comparable to the motion amplitude of 6.4 mm revealed by the lower row of images, which illustrate coronal views obtained using conventional methods.

Figure 6:
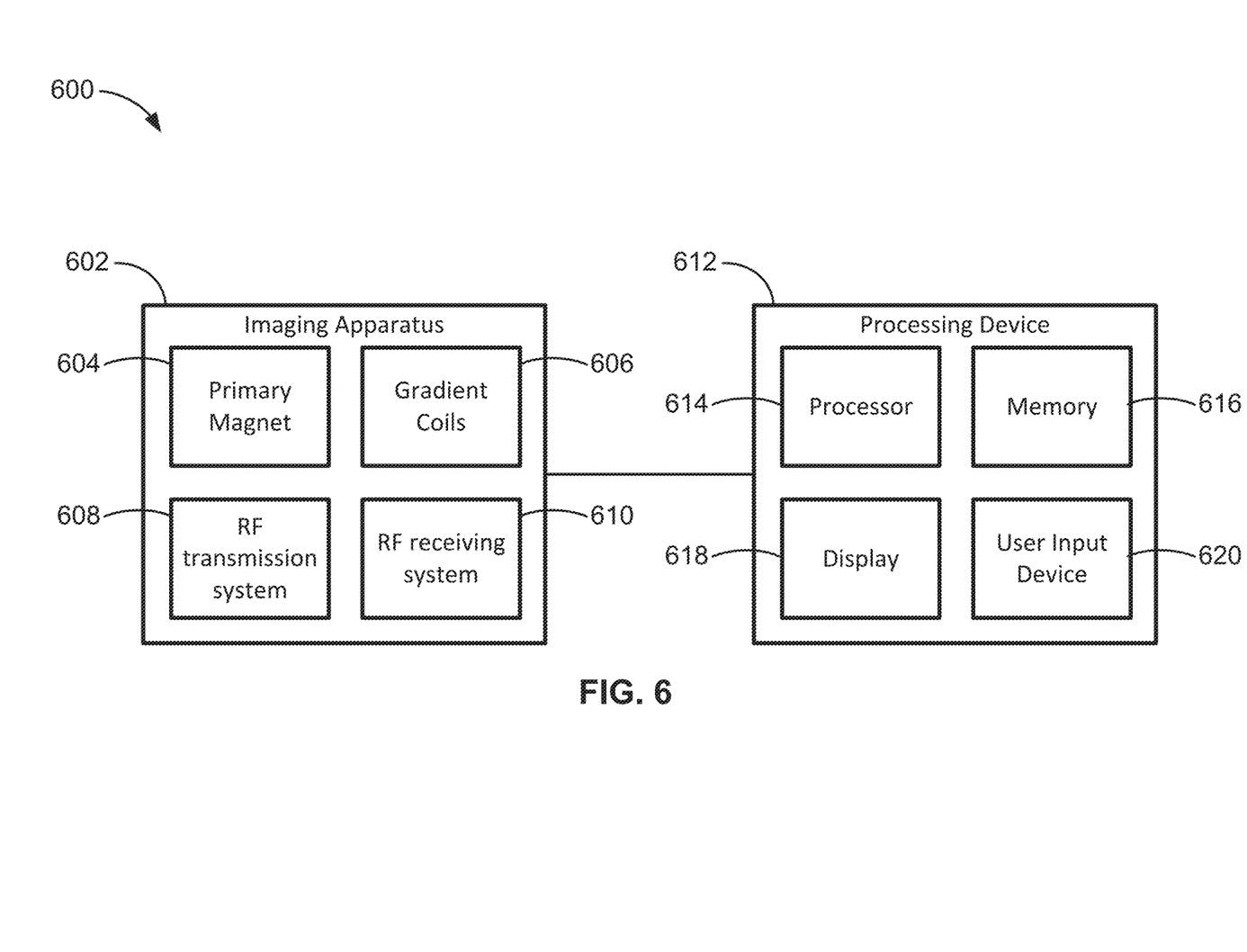
FIG. 6 illustrates a system for performing multidimensional magnetic resonance imaging, according to aspects of the present disclosure.

Aspects of the present disclosure can be implemented using a variety of hardware. One such implementation is illustrated in FIG. 6. A system 600 for performing magnetic resonance imaging on a subject includes an imaging apparatus 602, a first processing device 612, and a second processing device 622. The imaging apparatus 602 can be one used for standard magnetic resonance imaging, and can include a primary magnet 604, gradient coils 606, an RF transmission system 608, and an RF receiving system 610.

The primary magnet 604 can be a permanent magnet, an electromagnet (such as a coil), or any other suitable magnet. Primary magnet 604 is used to create the external magnet field that is applied to the sample during imaging. Gradient coils 606 create a secondary magnet field that distorts the external magnetic field and can cause the resonant frequency of the protons in the sample to vary by position. The gradient coils 606 can thus be used to spatially encode the positions of protons throughout the sample, e.g. can be used to select which plane intersecting the sample will be used for imaging. The RF transmission system 608 is used to apply the RF pulse sequence that provides energy to the protons in the sample to rotate their magnet moments out of alignment with the external magnetic field, and saturates the solute material protons. The RF transmission system 608 generally includes a frequency generator (such as an RF synthesizer), a power amplifier, and a transmitting coil. The RF receiving system 610 receives the signals emitted by the protons in the sample as they relax back to their standard alignment. The RF receiving system 610 can a receiving coil to receive the emitted signals, and a pre-amplifier for boosting the received signals and ensuring the signals are suitable for processing. In some implementations, the RF receiving system 610 can include a signal processing component that processes the received signals to provide data that is usable by the first processing device 612 and/or the second processing device 620. Each of the component of the imaging apparatus can be disposed within one or more housings.

The processing device 612 can be communicatively coupled to the imaging apparatus 602, and can include a processor 614, processor-executable memory 616, a display 618, and a user input device 620. The first processing device 612 is used to manage the operations of the imaging apparatus 602, and can thus be configured to cause the imaging apparatus 602 to perform multidimensional MRI imaging according to the principles disclosed herein. System 600 can also include one or more additional processing devices such that various tasks required to perform multidimensional MRI imaging can be performed by different processing devices. System 600 can also include one or more printers, one or more network interfaces, or one or more other types of hardware.

Aspects of the present disclosure can be implemented on a variety of types of processing devices, such as general purpose computer systems, microprocessors, digital signal processors, micro-controllers, application specific integrated circuits (ASICs), programmable logic devices (PLDs) field programmable logic devices (FPLDs), programmable gate arrays (PGAs), field programmable gate arrays (FPGAs), mobile devices such as mobile telephones, personal digital assistants (PDAs), or tablet computers, local servers, remote servers, wearable computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processing device, can be used for the memory or memories.

While aspects of the present disclosure have been described with reference to one or more particular implementations, those skilled in the art will recognize that many changes may be made thereto without departing from the spirit and scope of the present disclosure. Each of these implementations and obvious variations thereof are contemplated as falling within the spirit and scope of the present disclosure. It is also contemplated that additional implementations according to aspects of the present disclosure may combine any number of features from any of the implementations described herein.

REFERENCES

The following documents are provided to explain various aspects of the present invention. Their contents of each is hereby incorporated by reference herein in its entirety.

1. Christodoulou A G, Shaw J L, Nguyen C, Yang Q, Xie Y, Wang N, Li D. "Magnetic resonance multitasking for motion-resolved quantitative cardiovascular imaging," *Nature Biomed Eng.* 2018.

2. Stanisz G J, Odrobina E E, Pun J, Escaravage M, Graham S J, Bronskill M J, Henkelman R M. "T1, T2 relaxation and magnetization transfer in tissue at 3T," *Magn Reson Med* 2005.

What is claimed is:

1. A method of performing multidimensional magnetic resonance imaging on a subject, comprising:
    collecting imaging data for a region of interest of the subject, the imaging data related to one or more spatially-varying parameters of the subject within the region of interest;
    collecting auxiliary data for the region of interest in the subject, the auxiliary data related to one or more time-varying parameters of the subject within the region of interest;
    linking the imaging data and the auxiliary data;
    constructing one or more candidate image tensors, each of the one or more candidate image tensors having one or more temporal dimensions based on at least a portion of the linked imaging data and at least a portion of the linked auxiliary data;
    defining a cost function, the cost function taking a candidate image tensor of the one or more image tensors as an argument;
    determining a value of the cost function for each of the one or more candidate image tensors; and
    selecting as a final image tensor the candidate image tensor corresponding to a minimum value of the cost function,
    wherein the cost function penalizes discrepancies between (i) the candidate image tensor and (ii) the collected imaging data, the collected auxiliary data, or both the collected imaging data and the collected auxiliary data; and
    wherein the cost function penalizes larger values of (i) the rank of the candidate image tensor and (ii) the surrogate for the rank of the candidate image tensor.

2. The method of claim 1, wherein the one or more spatially-varying parameters include at least one of a $T_1$ relaxation parameter, a $T_2$ relaxation parameter, a contrast agent kinetic parameter, or a diffusion parameter.

3. The method of claim 1, wherein the imaging data is further indicative of motion of the region of interest of the subject.

4. The method of claim 1, wherein the auxiliary data is in the form of an external respiratory gating signal, a respiratory navigator signal, or training data.

5. The method of claim 4, wherein the training data includes a subset of the imaging data differing only in time.

6. The method of claim 5, wherein the subset of the imaging data is sampled at a rate sufficient to resolve motion of the region of interest.

7. The method of claim 1, wherein linking the imaging data and auxiliary data includes correlating a data point of the imaging data with at least one corresponding data point of the auxiliary data.

8. The method of claim 7, wherein the at least one corresponding data point of the auxiliary data is indicative of a time period in which the corresponding data point of the imaging data was measured.

9. The method of claim 8, wherein the at least one corresponding data point of the auxiliary data is indicative of the value of at least one of the one or more time-varying parameters during the time period within which the corresponding data point of the imaging data was measured.

10. The method of claim 1, wherein the final image tensor is a full-rank image tensor or a low-rank image tensor, and can be approximated by a low-rank image tensor, and wherein the final image tensor has (i) a minimum rank or (ii) a minimum value of a surrogate for the rank.

11. The method of claim 1, wherein the surrogate for the rank of each of the candidate image tensor measures how well the candidate image tensor can be approximated by a low-rank image tensor.

12. The method of claim 1, wherein the surrogate for the rank of each of the candidate image tensor is determined using a metric based on a nuclear norm, a Schatten p-norm, or a Ky Fan k-norm.

13. The method of claim 1, wherein the cost function is given by the equation $f(\chi)=\|d-E(\chi)\|_2^2+R(\chi)$.

14. The method of claim 1, wherein the cost function is minimized using a convex optimization technique.

15. The method of claim 14, wherein the convex optimization technique is an alternating direction of multipliers algorithm or a singular value thresholding algorithm.

16. The method of claim 1, wherein the cost function is minimized using a non-convex optimization technique.

17. The method of claim 16, wherein the convex optimization technique is power factorization.

18. The method of claim 1, wherein the final image tensor includes a dimension corresponding to each of the one or more spatially-varying parameters and a dimensions corresponding to each of the one or more time-varying parameters.

19. The method of claim 1, wherein the imaging data, the auxiliary data, or both the imaging data and the auxiliary data are obtained using a continuous acquisition mode or a semi-continuous acquisition mode.

20. The method of claim 1, wherein constructing the one or more candidate image tensors further comprises:
  identifying a plurality of tensor factors based on at least a portion of the collected imaging data and a portion of the collected auxiliary data; and
  combining at least a portion of the identified plurality of tensor factors.

21. A system for performing multidimensional magnetic resonance imaging, comprising:
  a magnet operable to provide a magnetic field;
  a transmitter operable to transmit to a region within the magnetic field;
  a receiver operable to receive a magnetic resonance signal from the region with the magnetic field; and
  a processor operable to control the transmitter and the receiver, the processor being configured to:
    collect imaging data for a region of interest of the subject, the imaging data related to one or more spatially-varying parameters of the subject within the region of interest;
    collect auxiliary data for the region of interest in the subject, the auxiliary data related to one or more time-varying parameters of the subject within the region of interest;
    link the imaging data and the auxiliary data;
    construct one or more candidate image tensors, each of the one or more candidate image tensors having one or more temporal dimensions based on at least a portion of the linked imaging data and at least a portion of the linked auxiliary data;
    define a cost function, the cost function taking a candidate image tensor of the one or more candidate image tensors as an argument;
    determine a value of the cost function for each of the one or more candidate image tensors; and
    select as a final image tensor the candidate image tensor corresponding to a minimum value of the cost function,
  wherein the cost function penalizes discrepancies between (i) the candidate image tensor and (ii) the collected imaging data, the collected auxiliary data, or both the collected imaging data and the collected auxiliary data; and
  wherein the cost function penalizes larger values of (i) the rank of the candidate image tensor and (ii) the surrogate for the rank of the candidate image tensor.

22. A non-transitory machine-readable medium having stored thereon instructions for performing multidimensional magnetic resonance imaging, which when executed by at least one processor, cause the at least one processor to:
  collect imaging data for a region of interest of the subject, the imaging data related to one or more spatially-varying parameters of the subject within the region of interest;
  collect auxiliary data for the region of interest in the subject, the auxiliary data related to one or more time-varying parameters of the subject within the region of interest;
  link the imaging data and the auxiliary data;
  construct one or more candidate image tensors, each of the one or more candidate image tensors having one or more temporal dimensions based on at least a portion of the linked imaging data and at least a portion of the linked auxiliary data;
  define a cost function, the cost function taking a candidate image tensor of the one or more candidate image tensors as an argument;
  determine a value of the cost function for each of the one or more candidate image tensors; and
  select as a final image tensor the candidate image tensor corresponding to a minimum value of the cost function,
  wherein the cost function penalizes discrepancies between (i) the candidate image tensor and (ii) the collected imaging data, the collected auxiliary data, or both the collected imaging data and the collected auxiliary data; and
  wherein the cost function penalizes larger values of (i) the rank of the candidate image tensor and (ii) the surrogate for the rank of the candidate image tensor.

* * * * *